US012673075B2

(12) United States Patent

Chen et al.

(10) Patent No.: US 12,673,075 B2
(45) Date of Patent: Jul. 7, 2026

(54) USE OF STREPTOCOCCUS THERMOPHILUS ST7 FOR MODULATING IMMUNITY AND AGAINST VIRUSES

(71) Applicant: Syngen Biotech Co., Ltd., Tainan City (TW)

(72) Inventors: Wei-Jen Chen, Tainan City (TW); Yu-Lun Tsai, Tainan City (TW); Gilbert Aaron Lee, Taipei City (TW)

(73) Assignee: Syngen Biotech Co., Ltd., Tainan City (TW)

( * ) Notice: Subject to any disclaimer, the term of this patent is extended or adjusted under 35 U.S.C. 154(b) by 285 days.

(21) Appl. No.: 18/393,021

(22) Filed: Dec. 21, 2023

(65) Prior Publication Data

US 2024/0207330 A1 Jun. 27, 2024

(30) Foreign Application Priority Data

Dec. 21, 2022 (TW) .................................. 111149133

(51) Int. Cl.
*A61K 35/741* (2015.01)
*A61P 1/00* (2006.01)
*A61P 37/04* (2006.01)

(52) U.S. Cl.
CPC .............. *A61K 35/741* (2013.01); *A61P 1/00* (2018.01); *A61P 37/04* (2018.01)

(58) Field of Classification Search
CPC ................................ A61K 35/741; A61P 1/00
See application file for complete search history.

(56) References Cited

PUBLICATIONS

Lee, Gilbert Aaron, et al. "Modulatory effects of heat-inactivated *Streptococcus thermophilus* strain 7 on the inflammatory response: A study on an animal model with TLR3-induced intestinal injury." Microorganisms 11.2 (2023): 278. (Year: 2023).*

* cited by examiner

*Primary Examiner* — Louise W Humphrey
*Assistant Examiner* — Candice Lee Swift
(74) *Attorney, Agent, or Firm* — MUNCY, GEISSLER, OLDS & LOWE, P.C.

(57) ABSTRACT

The present invention discloses use of *Streptococcus thermophilus* ST7 for modulating immunity, comprising using the *Streptococcus thermophilus* ST7 as an active ingredient for modulating immunity, wherein the *Streptococcus thermophilus* ST7 are deposited under the accession Nos. BCRC911126 and DSM34255. By administering an effective dose of *Streptococcus thermophilus* ST7 to an individual, the expression level of IL-12p40 on cells can be increased, the gut microbiota can be modulated and the Firmicutes/Bacteroidetes ratio in the intestine increases to improve immunity and antiviral ability.

4 Claims, 10 Drawing Sheets

A

B

C

USE OF STREPTOCOCCUS THERMOPHILUS ST7 FOR MODULATING IMMUNITY AND AGAINST VIRUSES

REFERENCE TO RELATED APPLICATIONS

The present application is based on, and claims priority from, Taiwan application number 111149133, filed Dec. 21, 2022, the disclosure of which is hereby incorporated by reference herein in its entirety.

BACKGROUND OF THE INVENTION

In modern society, pathogens that threaten humans include viruses, bacteria, and parasites, among which viruses are recognized to be the greatest threat. For example, the pandemic of coronavirus disease 2019 (COVID-19) has impacted the behavioral patterns of human society.

The immunity of human bodies is specialized in different directions. For example, T cell immunity can be tuned to favor the immunity of antiviral Th1, anti-fungal and -parasitic Th2, or Treg that suppresses autoimmune response, etc. Th1 immune response is known to help alleviate symptoms caused by viruses and shorten the duration of illness. Representative antiviral indicators of Th1 are IFN-γ and IL-12. It is known that edible microorganisms may have the ability to modulate the immune system, and the promotion mechanism is achieved by modulating the microbiota, or the active ingredients of microorganisms with immunomodulatory effect.

Among probiotic health foods, most probiotic supplements are provided to consumers in the form of live bacteria, mainly for following reasons: (1) It is generally believed that only live bacteria have the ability to modulate microbiota; (2) Active ingredients of probiotics that modulate the immune system may be metabolites of live bacteria; and (3) It may cause active ingredients that modulate immunity to lose activity during processing to inactivate. However, it is troubling that the number of live bacteria in probiotics will decrease rapidly when stored at room temperature, and the function of live bacteria after death has been questioned.

The presence of viruses in enterocytes can be detected in a variety of ways, for example using toll-like receptors (TLRs) in the family of pattern recognition receptors to recognize double-stranded RNAs (dsRNAs) in the viral genome or dsRNAs during viral replication and trigger subsequent immune responses. Polyinosinic acid-polycytidylic acid (hereinafter referred to as poly I:C for short) is a synthetic dsRNA analogue. TLR3 can recognize poly I:C and dsRNA, subsequently activate NF-kB, and exhibit an inflammatory response. In an animal model of poly I:C-induced intestinal injury, the intraperitoneal administration of poly I:C triggered an intestinal immune response and caused severe mucosal damage in the intestine in a TLR3-dependent manner.

However, among the existing probiotic technologies for modulating immunity, there is a lack of probiotics that have the efficacy of significantly increasing the expression level of IL-12p40 in cells, modulating the intestinal microbiota and increasing a Firmicutes/Bacteroidetes ratio (F/B ratio) in the intestine at the same time to improve the immunity and antiviral ability. In addition, among the existing probiotic technologies for modulating immunity, most of them employ composite strains of a plurality of live bacteria of probiotics. Currently, there is no single strain of probiotics in an inactivated state that can be used to simultaneously improve immunity (antiviral ability) and modulate the intestinal microbiota.

FIELD OF THE INVENTION

The present invention relates to a use of probiotics, more particular the use of Streptococcus thermophilus ST7 for modulating immunity and against viruses.

SUMMARY OF THE INVENTION

In view of this, the inventors of the present invention have a deep understanding of the shortcomings and deficiencies of the previous applications and are eager to make improvements and innovations. After years of research, we finally successfully isolate probiotics that can greatly increase the expression level of IL-12p40 in cells, modulate the intestinal microbiota, increase a Firmicutes/Bacteroidetes ratio in the intestine to improve immunity and antiviral ability, and also provide a novel and low-cost health care strategy of modulating immunity using probiotics.

An object of the present invention is to provide a use of Streptococcus thermophilus ST7 in the preparation of a pharmaceutical composition for modulating immunity, comprising using Streptococcus thermophilus ST7 as an active ingredient that modulates immunity, wherein the Streptococcus thermophilus strain ST7 is deposited under the accession Nos. BCRC911126 and DSM34255.

In an embodiment of the present invention, Streptococcus thermophilus ST7 is an inactivated bacterium.

In an embodiment of the present invention, the pharmaceutical composition is free of other species than Streptococcus thermophilus ST7.

In an embodiment of the present invention, Streptococcus thermophilus ST7 is useful for increasing the expression level of IL-12p40 in cells, and the expression level of IL-12p40 is 400 pg/mL to 1000 pg/mL.

In an embodiment of the present invention, Streptococcus thermophilus ST7 is useful for modulating intestinal microbiota and increasing a Firmicutes/Bacteroidetes ratio in the intestine thereby improving immunity.

In an embodiment of the present invention, Streptococcus thermophilus ST7 is useful for improving the antiviral ability.

In an embodiment of the present invention, the antiviral ability is to alleviate intestinal injury caused by viruses and enhance antiviral immunity.

In an embodiment of the present invention, the antiviral ability is to increase the activation of CD4$^+$ T cells and CD8$^+$ T cells during viral infection.

In an embodiment of the present invention, the antiviral ability is to induce the expression of IFN-γ in CD4$^+$ T cells and CD8$^+$ T cells.

In an embodiment of the present invention, Streptococcus thermophilus ST7 is administered at a dose of 1×10$^6$ to 1×10$^{10}$ CFU/day.

In summary, the live bacteria of Streptococcus thermophilus ST7 used in the present invention can induce a higher level of antiviral indicator IL-12p40 than other strains of the same species, and especially after heat inactivation, the effect is more prominent. Surprisingly, in the experiment that simulate viral infection by intraperitoneally injecting the mouse dsRNA viral mimic poly I:C, the inactivated bacteria of Streptococcus thermophilus ST7 not only improved the antiviral indicator IFN-γ and T cell antiviral ability but also alleviated intestinal injury and changed the intestinal micro-
biota, showing a surprising antiviral potential.

BRIEF DESCRIPTION OF THE DRAWINGS

The techniques of present invention would be more
understandable from the detailed description given herein
below and the accompanying figures are provided for better
illustration, and thus description and figures are not limita-
tive for present invention, and wherein:

FIG. 6 shows statistical charts illustrating the effect of
*Streptococcus thermophilus* ST7 on the intestinal microbiota
in animal experiments, wherein FIG. 6A shows the Alpha
diversity; and FIGS. 6B and 6C show the Beta diversity of
different groups.

DETAILED DESCRIPTION OF THE INVENTION

Definitions of Terms

Figure 1:
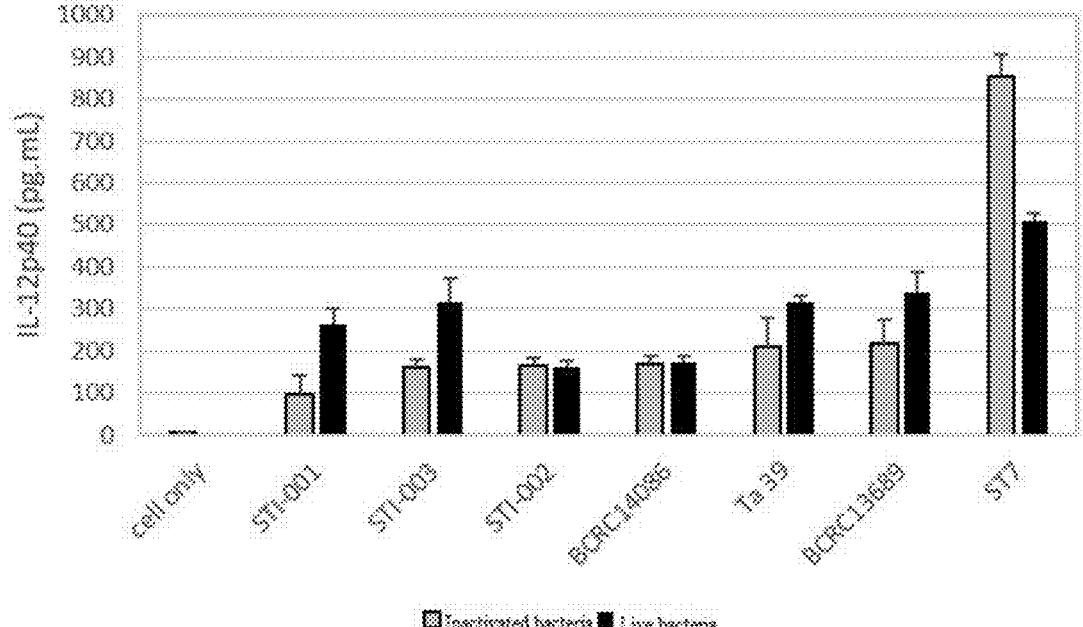
FIG. 1 is a bar graph illustrating the comparison of the
expression levels of antiviral indicator IL-12p40 in cells
induced by different strains of *Streptococcus thermophilus*.

Many technical and scientific terms commonly used in the
field of biotechnology are widely used in this specification.
In the following description, the following definitions are
provided for the purpose of providing a clear and consistent
understanding of this specification and the scope of the
patent application, as well as the scope given to such terms.
Other terms that are not specifically defined below have
meanings that are commonly understood by those skilled in
the art.

The materials used in the present invention are all com-
mercially and easily available materials, unless otherwise
specified. The *Streptococcus thermophilus* strain ST7 used
in the embodiments of the present invention is deposited
with the Food Industry Research and Development Institute
in Hsinchu, Taiwan, under the accession No. BCRC 911126;
and the German Collection of Microorganisms and Cell
Cultures (DSMZ) under the accession No. DSM34255.

The terms "or", "as well as" and "and" used in this
specification all refer to "or/and", unless otherwise stated. In addition, the phrases "comprise", "comprising" and
"include", "including" are open-ended connectors without
constraints. The foregoing paragraphs are only systematic
references and should not be construed as limitations to the
subject matters of the invention.

"%" used in this specification refers to "weight percentage
(wt %)" unless otherwise specified; a numerical range (e.g.,
10%-11% of A) includes the upper and lower limits (i.e.,
$10\% \le A \le 11\%$) unless otherwise specified; if a numerical
range does not define the lower limit (e.g., B less than 0.2%,
or B below 0.2%), it means that the lower limit may be 0 (i.e.
$0\% \le B \le 0.2\%$); the proportion of "weight percentage" of
each component can also be replaced by the proportion of
"parts by weight".

All values disclosed in this specification are subject to a
standard technical error of measurement (standard devia-
tion) of ±10%. The word "about" is intended to represent
±10%, ±5%, ±2.5%, or ±1% relative to a given value. In
other words, "about 20%" means 20±2%, 20±1%, 20±0.5%,
or 20±0.25%.

"Modulating immunity" used in this specification refers to
increasing or decreasing the immune response specifically or
non-specifically, or refers to suppressing allergic responses
or autoimmune responses while retaining or even enhancing
resistance to foreign invaders or cancer cells.

"A pharmaceutical composition" as used in this specifi-
cation refers to a solid or liquid composition in a form,
concentration and purity suitable for administration to
patients, which can induce desired physiological changes
after administration; the pharmaceutical composition is ster-
ile and/or non-pyrogenic.

"An individual" used in this specification refers to any
mammal that needs or is considered to potentially need a
composition of *Streptococcus thermophilus* ST7 of the pres-
ent invention, including primates, rodents, pets, laboratory
animals, and domesticated wild animals. For example, an
individual may include, but is not limited to: monkeys,
humans, pigs, cattle, sheep, goats, equidae, mice, rats,
guinea pigs, hamsters, rabbits, felines, and canines. Prefer-
ably, the individual is a mouse or human.

"An effective amount", "a dose" and similar terms used in
this specification refer to an amount of a medicament that is
used herein to treat, cure, prevent, or ameliorate a disease,
disorder, or side effect, or to slow the progression rate of a
disease or disorder. The term within its scope also includes
an amount that effectively enhances normal physiological
functions.

"Pharmaceutically acceptable" as used in this specifica-
tion refers to a substance or composition that must be
compatible with other ingredients of a pharmaceutical for-
mulation and does not aggravate symptoms in a patient.

Utilizing the techniques well known to those with ordi-
nary knowledge in the technical field to which the present
invention belongs, the pharmaceutical composition provided
by the present invention can be prepared into a dosage form
suitable for the compositions of the present invention by
combining the active ingredients or composition provided
herein with at least one pharmaceutically acceptable vehicle.
The dosage form includes, but is not limited to, a solution,
a suspension, a powder, a tablet, a buccal troche, a pill, a
chewing gum, a capsule, and other oral dosage forms similar
to or suitable for use in the present invention.

The "pharmaceutically acceptable vehicle" used in this
specification includes one or more ingredient types selected
from a solvent, an emulsifier, a suspending agent, a disin-
tegrant, a binder, an excipient, a stabilizer, a chelating agent, a diluent, a gelatinizer, a preservative, a lubricant, a surfactant, and other oral vehicles similar to or suitable for use in the present invention.

In the aforementioned composition, one or more dissolution aids, buffers, colorants, flavoring agents, etc. which are commonly used in the field of preparations may also be properly added as needed.

"Pharmaceutically acceptable excipient" used in this specification includes, but is not limited to, at least one of a polymer, a resin, a plasticizer, a filler, a lubricant, a diluent, a binder, a disintegrant, a solvent, a co-solvent, a surfactant, a preservative, a sweetener, a flavoring agent, a pharmaceutical grade dye or pigment, and a viscosity agent.

[*Streptococcus thermophilus* ST7]

The *Streptococcus thermophilus* strain ST7 used in the present invention was deposited with the Food Industry Research and Development Institute in Hsinchu, Taiwan, under the accession No. BCRC 911126 on Apr. 25, 2022; and the German Collection of Microorganisms and Cell Cultures (DSMZ) under the accession No. DSM34255.

In an embodiment, *Streptococcus thermophilus* ST7 may be a fermentation product thereof, for example, a metabolite of *Streptococcus thermophilus* ST7. In an embodiment, *Streptococcus thermophilus* ST7 may be a live or inactivated bacterium, but from the perspective of improving immunity, *Streptococcus thermophilus* ST7 is preferably an inactivated bacterium, and more preferably a heat-killed bacterium.

The present invention uses *Streptococcus thermophilus* ST7 as an active ingredient that modulates immunity. The types of an active ingredient are not limited, for example, *Streptococcus thermophilus* ST7 may be used in combination with one or more other probiotic species or strains to form a probiotic composition, or *Streptococcus thermophilus* ST7 may be used as the only active ingredient. In an embodiment, from the standpoint of production cost, the active ingredient that modulates immunity preferably only includes *Streptococcus thermophilus* ST7. In other words, in the use of the *Streptococcus thermophilus* strain ST7 of the present invention in the manufacture of a medicament for modulating immunity, the pharmaceutical composition is preferably free of other strains or species than *Streptococcus thermophilus* ST7.

[Methods for Improving Immunity]

The present invention also discloses a method for improving immunity using *Streptococcus thermophilus* ST7. The method involves administering an effective amount of *Streptococcus thermophilus* ST7 to an individual in need thereof, wherein the *Streptococcus thermophilus* strain ST7 is deposited under the accession numbers BCRC911126 and DSM34255.

The method for improving immunity of the present invention involves administering *Streptococcus thermophilus* ST7 to an individual (e.g., a human individual) to modulate immunity. The method for improving immunity according to the present invention is also suitable for increasing the expression level of IL-12p40 in cells, modulating the intestinal microbiota (increasing the abundance of Firmicutes and Bacteroidetes in the intestine), and improving antiviral ability (mitigating intestinal injury caused by viruses, increasing the activation of CD4$^+$ T cells and CD8$^+$ T cells, inducing the expression of IFN-$\gamma$ in CD4$^+$ T cells and CD8$^+$ T cells) in an individual.

In an embodiment, the *Streptococcus thermophilus* strain ST7 of the present invention induces the expression of the antiviral indicator IL-12p40 in cells in a level of about 400 pg/mL to 1000 pg/mL, for example, about 450 pg/mL, 500 pg/mL, 550 pg/mL, 600 pg/mL, 650 pg/mL, 700 pg/mL, 750 pg/mL, 800 pg/mL, 850 pg/mL, 900 pg/mL, 950 pg/mL, and a range between any two of the above values. The *Streptococcus thermophilus* strain ST7 of the present invention has an outstanding effect in inducing the expression of IL-12p40 over other *Streptococcus thermophilus* strains.

[Administration of *Streptococcus thermophilus* ST7]

Suitable routes of administration for the pharmaceutical composition provided by the present invention include, but are not limited to, oral, intravenous, rectal, aerosol, gastrointestinal, ocular, pulmonary, transmucosal, transdermal, vaginal, auricular, nasal, or topical administration. Additionally, examples of gastrointestinal administration include, but are not limited to, intramuscular, subcutaneous, intravenous, intramedullary, and intrathecal, intraventricular, intraperitoneal, intralymphatic, or intranasal injection. The dosage form of the pharmaceutical composition provided by the present invention can be adjusted properly as desired without particular limitations. An oral dosage form is preferred.

[Dose of *Streptococcus thermophilus* ST7]

In the method for improving immunity of the present invention, an effective amount of *Streptococcus thermophilus* ST7 is administered to an individual in need thereof. Specifically, the dose can vary with the purpose of administration, the health and physical conditions of an individual in need thereof, age, the taxon of an individual in need thereof (such as humans, non-human primates, primates, etc.), the dosage form of *Streptococcus thermophilus* ST7, assessment of medical situations made by treating clinicians and other relevant factors. The dose is expected to fall within a relatively wide range, which can be determined via conventional experiments.

In an embodiment, different doses of *Streptococcus thermophilus* ST7 can be used as desired, usually from about $1\times10^6$ to $1\times10^{10}$ CFU/day, for example, about $5\times10^6$, $1\times10^7$, $5\times10^7$, $1\times10^8$, $5\times10^8$, $1\times10^9$, or $5\times10^9$ CFU/day, and a range between any two of the aforementioned values.

In an embodiment, different administration cycles of *Streptococcus thermophilus* ST7 can be used as desired, usually from about 2 days to 4 months or longer. For example, the administration cycle may be about 2, 4, 6, 8, 10, 15, 20, 25, 30, 35, 40, 45, 50, 55, or 60 days. Alternatively, the administration cycle may be about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks or longer.

In an embodiment, different administration frequencies of *Streptococcus thermophilus* ST7 can be used as desired. For example, it may be administered about 1 to 3 times a day, 1 to 6 times in two days, 1 to 9 times in three days, 1 to 14 times a week, or 1 to 60 times a month.

An edible material may be further added to the pharmaceutical composition provided by the present invention to prepare a food product or health care product. The edible material includes, but is not limited to, water, fluid milk products, milk, concentrated milk, yogurt, sour milk, frozen yogurt, lactic acid bacteria-fermented beverages, milk powder, ice cream, cream cheeses, dry cheeses, soybean milk, fermented soybean milk, vegetable-fruit juices, juices, sports drinks, confectionery, jellies, candies, infant formulas, health foods, animal feeds, Chinese herbals or dietary supplements.

Several embodiments and comparative embodiments are described below to illustrate the use of the *Streptococcus thermophilus* strain ST7 of the present invention for modulating immunity. However, they are not intended to limit the present invention. Any of those skilled in the art would make various alterations and modifications without departing from the spirit and scope of the present invention.

The data in the following embodiments were analyzed by Mann-Whitney t tests and one-way ANOVA using Prism software (GraphPad, USA). The error bars in the results represent the standard errors of the mean (SEM). Microbiota enrichment analysis was conducted using the linear discriminant analysis (LDA) effect size (LEfSe) method. Data were compared using the Kruskal-Wallis and Wilcoxon tests. It was considered as significant at p≤0.05, with a log LDA score of ≥2.

Embodiment 1: Preparation of Biological Material

The *Streptococcus thermophilus* strain ST7 can be cultured in a general growth medium, e.g., a medium containing about 1-2% glucose, about 1-2% peptone, about 0.01-0.08% magnesium sulfate, etc. Other *Streptococcus thermophilus* strains used in the following embodiments are those easily available to those with ordinary knowledge in the technical field to which the present invention belongs, and therefore do not need to be deposited.

Embodiment 2: Expression Level of Antiviral Indicator IL-12p40 Significantly Induced by *Streptococcus thermophilus* Strain ST7 in Cells In order to illustrate that the *Streptococcus thermophilus* strain ST7 of the present invention has a better immunomodulatory efficacy compared to other *Streptococcus thermophilus* strains, and to illustrate whether live or inactivated bacteria of each strain of *Streptococcus thermophilus* affect its immunomodulatory efficacy, in this example, different *Streptococcus thermophilus* strains STI-001, STI-002, STI-003, Ta 39, BCRC14086, BCRC13689, ST7, etc. were selected, and each of the above strains was divided into a live bacteria group and an inactivated bacteria group for experiments. The specific experimental methods are as follows:

After about 50% Brain Heart Infusion broth (BHI broth) and about 50% MRS (DeMan-Rogosa-Sharpe) broth were mixed, each of the above-mentioned *Streptococcus thermophilus* strains was cultured with the mixed broth at about 37° C. Samples were collected in the early stage of the stationary phase, centrifuged, and washed with about 0.9% NaCl solution, and then resuspended in about 0.9% NaCl solution to afford live bacteria. Live bacteria were heated at about 70° C. for about 30 min to form inactivated bacteria (heat-killed bacteria).

The mouse macrophage J774A.1 cell line (BCRC 60140) purchased from the Bioresource Collection and Research Center was used and cultured in DMEM (Dulbecco's Modified Eagle Medium) containing about 10% fetal bovine serum at about 37° C. with 5% $CO_2$. About $4\times10^4/100$ µL of J774A.1 cells were added to a 96-well plate for culture, and then about $2\times10^5/50$ µL of each of *Streptococcus thermophilus* strains were added, while the control group was added with J774A.1 cells alone without any *Streptococcus thermophilus*. About 24 h after the addition of *Streptococcus thermophilus* strains, the supernatants were collected to determine the IL-12p40 level using an enzyme immunosorbent assay (ELISA) kit.

Referring to FIG. 1, it shows the level of the antiviral indicator IL-12p40 expressed in cells induced by different *Streptococcus thermophilus* strains. It can be seen from the figure that compared with the ordinary *Streptococcus thermophilus* strain STI-001, STI-002, STI-003, BCRC14086, Ta 39, or BCRC13689, the *Streptococcus thermophilus* strain ST7 of the present invention can significantly increase the level of the antiviral indicator IL-12p40 expressed in cells. Accordingly, it is demonstrated that the *Streptococcus thermophilus* strain ST7 of the present invention has a better immunomodulatory efficacy than other *Streptococcus thermophilus* strains.

Moreover, it can be seen from FIG. 1 that the *Streptococcus thermophilus* strain ST7 of the present invention has a significant immunomodulatory efficacy without the need to add other strains. That is, the present invention provides a novel and low-cost health care strategy of probiotic immunomodulatory ability without the need to comprise strains or species other than *Streptococcus thermophilus* ST7.

In addition, it can be seen from FIG. 1 that there was a tendency for live bacteria of the ordinary *Streptococcus thermophilus* strain STI-001, STI-002, STI-003, BCRC14086, Ta 39, or BCRC13689 to induce higher expression levels of antiviral indicator IL-12p40 in J774A.1 macrophages compared with inactivated bacteria. To the contrary, for the *Streptococcus thermophilus* strain ST7 of the present invention, inactivated bacteria induced a significantly higher expression level of antiviral indicator IL-12p40 in J774A.1 macrophages. Hence, it is demonstrated that the *Streptococcus thermophilus* strain ST7 of the present invention has very different immunomodulatory properties from ordinary *Streptococcus thermophilus* strains, and that the inactivated bacteria of the *Streptococcus thermophilus* strain ST7 of the present invention has a better immunomodulatory efficacy. Therefore, the following experiments were conducted with inactivated bacteria of *Streptococcus thermophilus* ST7.

The *Streptococcus thermophilus* strains other than *Streptococcus thermophilus* ST7 used in the embodiments of the present invention were used as comparative examples. These strains (STI-001, STI-002, STI-003, BCRC14086, Ta 39, and BCRC13689) should not be used as the basis for judging whether the present invention can be achieved. If necessary, *Streptococcus thermophilus* strains commercially available or obtained from other approaches may also be used to replace these strains. Using *Streptococcus thermophilus* strains commercially available or obtained from other approaches to replace these strains (STI-001, STI-002, STI-003, BCRC14086, Ta 39, and BCRC13689) as comparative embodiments does not affect the implementation of the present invention.

Embodiment 3: Animal Experiment Design

First, 8-week-old C57BL/6JNarl male mice (purchased from the National Laboratory Animal Center, Taiwan) were prepared and housed under specific pathogen-free conditions. All mice were fed a conventional balanced diet ad libitum for 7 days. Next, referring to FIG. 2, it is a diagram of animal experimental design of the present invention. As shown in the figure, the day after 7 days of a conventional balanced diet ad libitum was considered as day 0, and then the mice were divided into three groups, namely the control group, the poly I:C group, and the poly I:C+ST7 group, in all of which the mice were fed a conventional balanced diet ad libitum.

Figure 2:
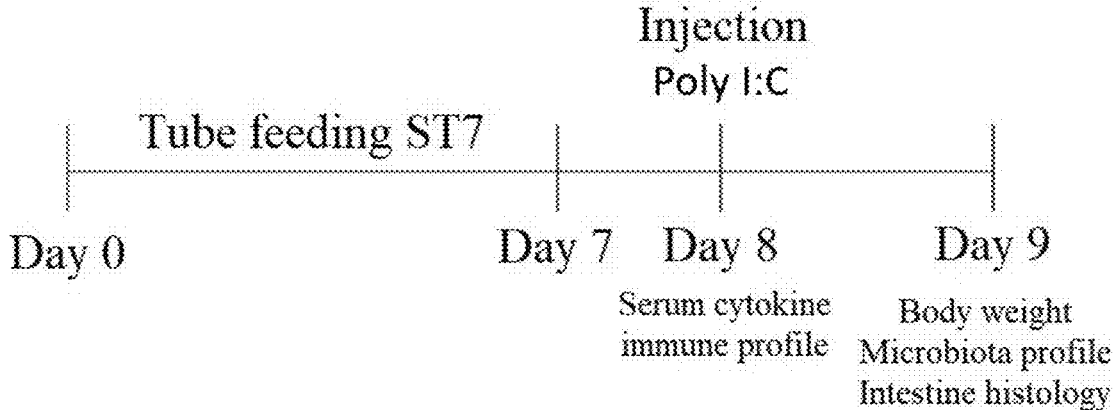
FIG. 2 is a diagram of animal experimental design of the
present invention.

Referring to FIG. 2, in the control group the mice were tube-fed with pure water from day 0 to day 7 and intraperitoneally injected with about 100 µg/g of phosphate-buffered saline (PBS) on day 8. Blood was collected 2 h later for biochemical analysis. In the poly I:C group, the mice were tube-fed with pure water from day 0 to day 7, and intraperitoneally injected with about 100 µg/g poly I:C on day 8. Blood was collected 2 h later for biochemical analysis. In the poly I:C+ST7 group, the mice were tube-fed with $10^7$ cells/mouse/day of inactivated bacteria of *Streptococcus thermophilus* ST7 from day 0 to day 7 and were intraperitoneally injected with about 100 µg/g poly I:C on day 8. Blood was collected 2 h later for biochemical analysis. All three groups were weighed on day 9, and intestinal tissues (such as feces in the small intestine and cecum) were collected and stored at −80° C. for microbiota analysis; wherein the serum was stored at −80° C., and the serum IFN-γ level was analyzed using a commercially available ELISA kit.

Embodiment 4: Poly I:C-Induced Weight Loss Alleviated by *Streptococcus thermophilus* ST7

Figure 3:
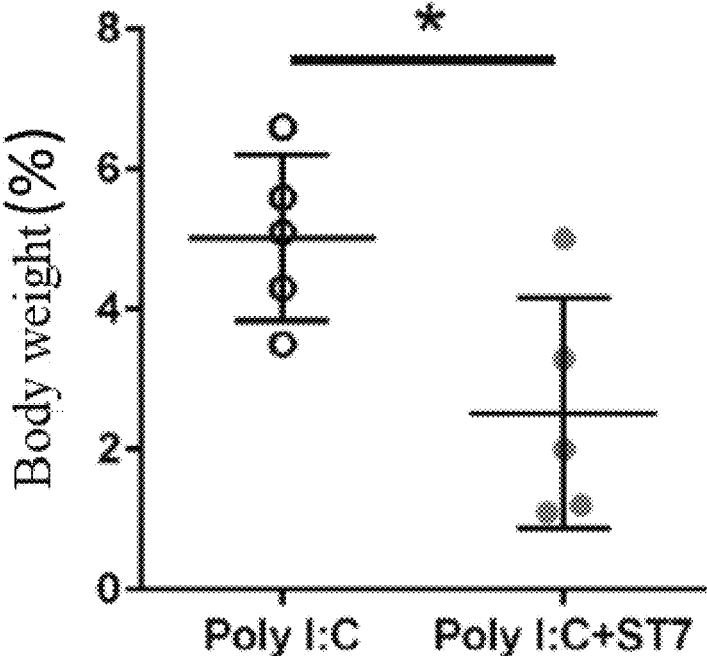
FIG. 3 is a scatter plot illustrating the effect of *Strepto-
coccus thermophilus* ST7 on body weight changes in animal
experiments.

Referring to FIG. 3, it shows that *Streptococcus thermophilus* ST7 affects the body weight of mice, presented in the form of the percentage of weight loss compared to the control group of mice, n=5, *P<0.05. As shown in the figure, poly I:C was used to simulate viral infection. The viral infection group treated with poly I:C caused weight loss (about 5%) in mice. On the other hand, the poly I:C+ST7 dosing group significantly alleviated the weight loss (about 2%) caused by viruses. Therefore, the *Streptococcus thermophilus* strain ST7 of the present invention can alleviate the weight loss caused by viruses and has the efficacy of ameliorating viral symptoms.

Embodiment 5: Poly I:C-Induced Small Intestinal Injury Alleviated by *Streptococcus thermophilus* ST7

Histopathological Evaluation Method of Small Intestine: Small intestine samples were excised, washed with PBS, and immersed in a formalin solution. After fixation, the samples were dehydrated, embedded, cut into sections, and stained with hematoxylin and eosin (H&E). For pathological score and villus length, please refer to the following technical literatures:

Int J Clin Exp Pathol 2014, 7, 4557-4576.

PLoS One 2014, 9, e110549, doi:10.1371/journal.pone.0110549.

Figure 4:
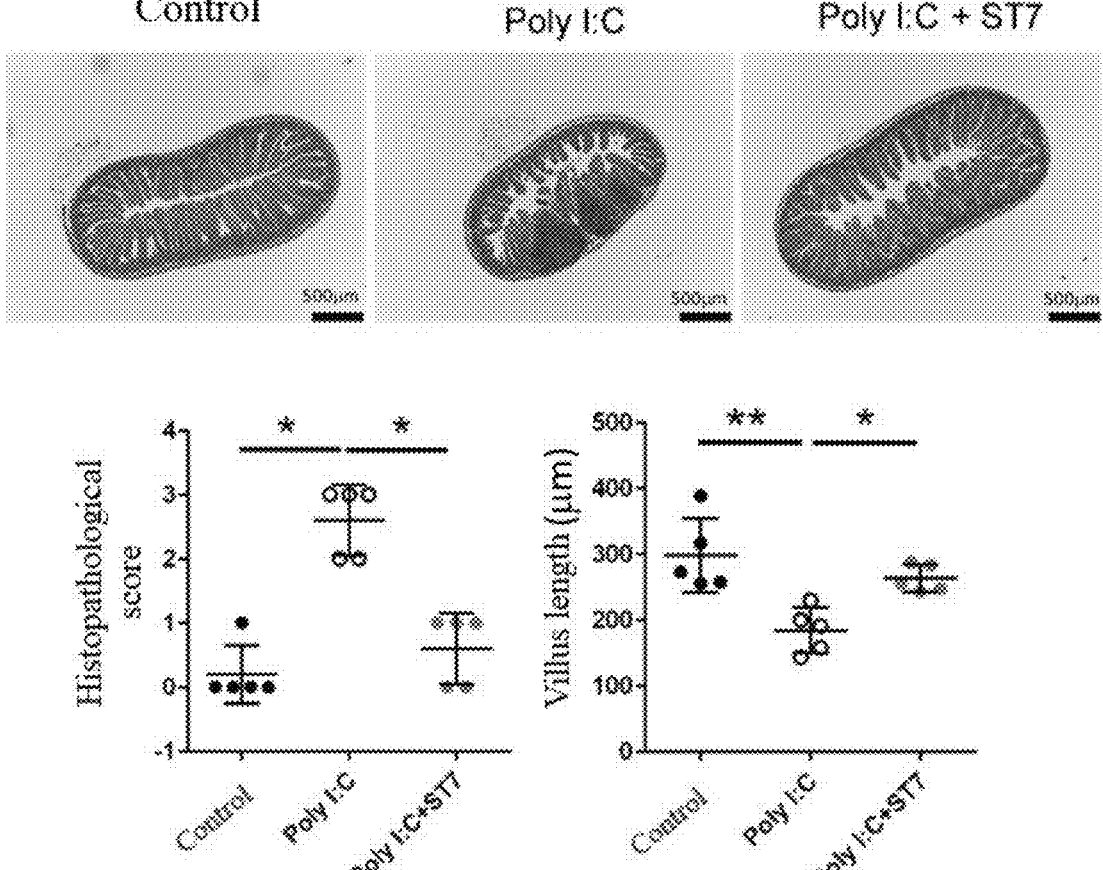
FIG. 4 shows a pathological tissue diagram and scatter
plots illustrating the effect of *Streptococcus thermophilus*
ST7 on small intestinal pathology in animal experiments.

Referring to FIG. 4, it shows that *Streptococcus thermophilus* ST7 affects the pathology of the small intestine. The upper panel of FIG. 4 is a pathology image of the small intestine sectioned and stained with hematoxylin and eosin. The lower left panel shows the pathological score of the small intestine tissue. The lower right panel shows the length of the small intestinal villi, n=5, *P<0.05, **P<0.01. As shown in the figure, the viral infection group treated with poly I:C induced the small intestinal tissue inflammation and villus shortening in the mice. On the other hand, the poly I:C+ST7 dosing group significantly reduced the small intestinal inflammation and villus shortening caused by viruses. Therefore, the *Streptococcus thermophilus* strain ST7 of the present invention can alleviate the intestinal injury caused by viruses through TLR3 and has the efficacy of ameliorating viral symptoms.

Embodiment 6: Expression Level of Poly I:C-Stimulated IFN-γ Significantly Increased by *Streptococcus thermophilus* ST7

Analysis of the expression level of IFN-γ: Cells were incubated in RPMI medium containing 100 ng/mL phorbol myristate acetate, 1 µg/mL an ionophore A23187 and 10% fetal bovine serum (FBS) for 3 h. Then 5 µg/mL Brefeldin A was added and cultured for 2 h. The cells were stained for T-cell-related surface markers, and intracellularly stained with an IFN-γ-APC (XMG1.2) or an isotype control, and were subsequently analyzed using flow cytometry.

Figure 5:
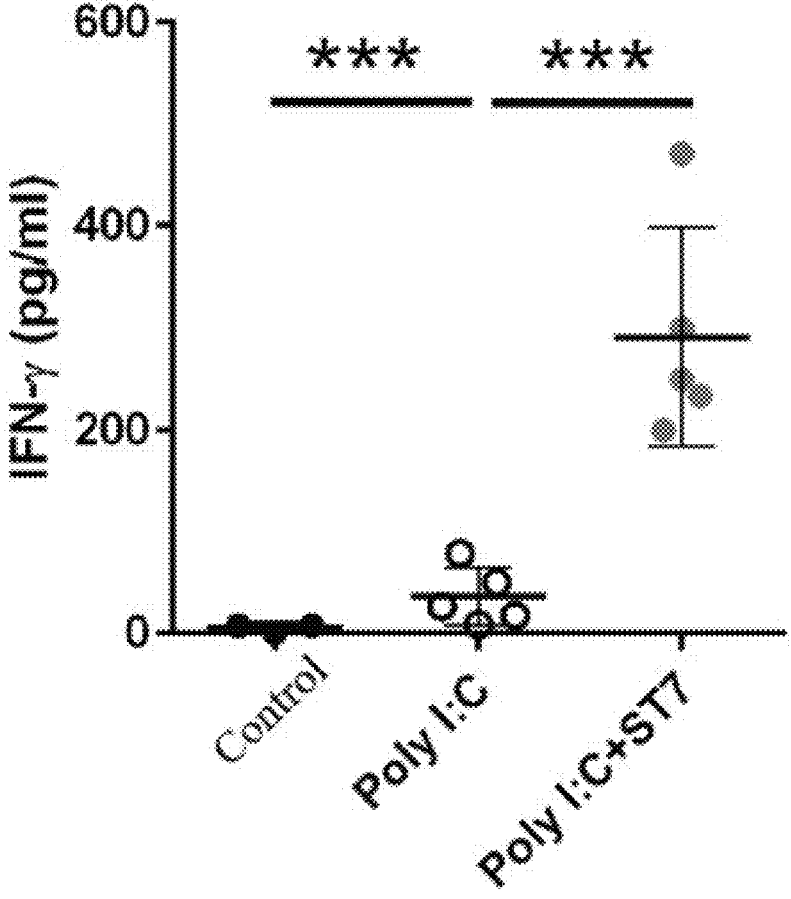
FIG. 5 is a scatter plot illustrating the effect of *Strepto-
coccus thermophilus* ST7 on the IFN-γ level in blood in
animal experiments.

Referring to FIG. 5, it shows that *Streptococcus thermophilus* ST7 affects the IFN-γ level in the blood, ***P<0.001. As shown in the figure, the viral infection group treated with poly I:C stimulated the generation of serum IFN-γ in mice. On the other hand, the poly I:C+ST7 dosing group significantly increased the level of the serum IFN-γ stimulated by the virus. Therefore, intake of the *Streptococcus thermophilus* strain ST7 of the present invention can enhance antiviral immunity.

Embodiment 7: Poly I:C-Stimulated Intestinal Microbiota Modulated by *Streptococcus thermophilus* ST7

In order to demonstrate that *Streptococcus thermophilus* ST7 can affect the intestinal microbiota of mice, this experiment detected the Alpha diversity of the microbiota in feces of mice in each group. The method was to use the commercially available QIAamp Fast DNA Stool Mini Kit (Qiagen, Germany) to extract DNA from mouse feces, and then use the universal primer pair 341F and 805R of the Illumina MiSeq system to amplify the V3-V4 region of bacterial 16S rRNA genes. Redundant sequencing reads were removed using Cutadapt (v1.12). Filtered sequencing sequences were processed using the DADA2 package (v1.14.1) in R software (v3.6.1). The V3-V4 sequence variations in the samples were inferred using the DADA2 package, and the frequency of each sequence in each sample was determined. The taxonomy assignment was conducted using the SILVA database (v138). Sequence alignment and phylogenetic tree drawing were performed using DECIPHER (v2.14.0) and phangorn software (v2.14.0), and taxon analysis was performed using phyloseq software (v1.30.0). Alpha diversity indices were calculated to estimate the richness of species. Statistical analyses were performed using the Wilcoxon-Mann-Whitney test (α=0.05). For more detailed test methods, please refer to the following technical literature: Brain Sci 2021, 11, doi:10.3390/brainsci11081085.

Figure 6:
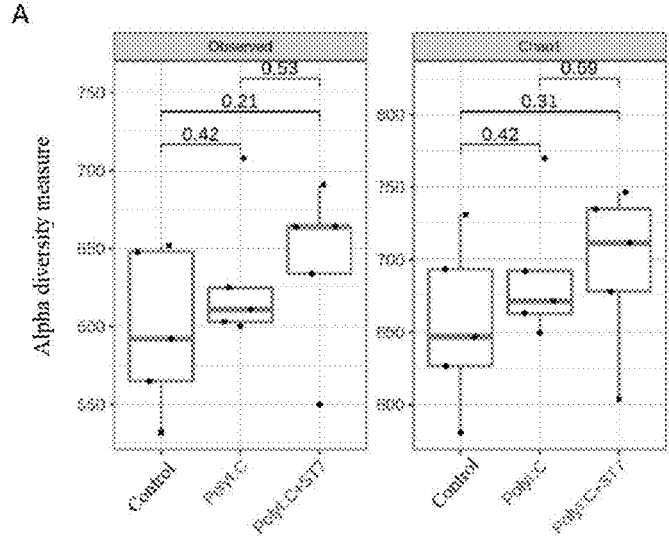
Figure 6:
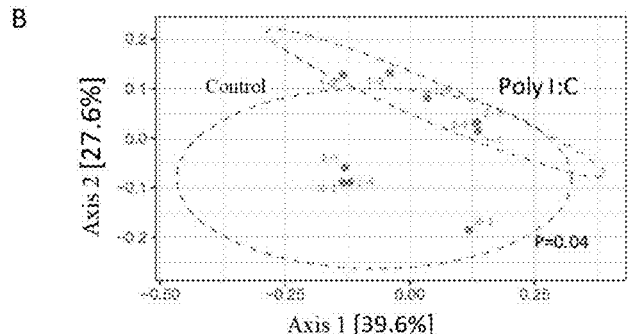
Figure 6:
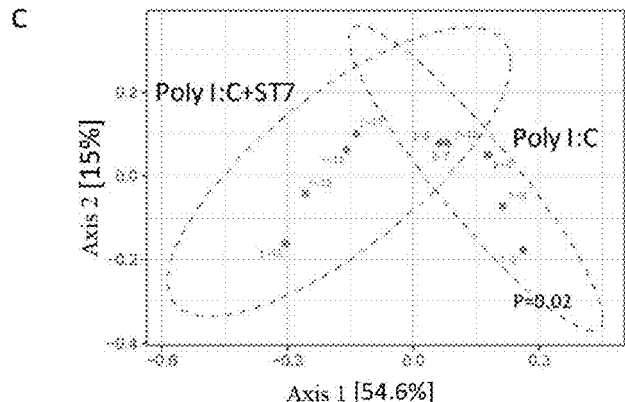

Referring to FIG. 6, it shows that *Streptococcus thermophilus* ST7 affects the intestinal microbiota in mice. Samples were taken from feces of the mice in each group to detect the distribution of fecal microbiome. FIG. 6A suggests that the alpha diversity of the microbiome in each group was similar. However, as shown in FIG. 6B, compared with the mice in the control group the viral infection group treated with poly I:C had a considerably altered fecal microbiota profile, which affected the beta diversity. FIG. 6C shows that the poly I:C+ST7 dosing group administrated with the *Streptococcus thermophilus* strain ST7 of the present invention further altered the microbiota profile.

FIG. 6B is described more specifically below, which is a principal component analysis graph of mice in the control group, the viral infection group treated with poly I:C, and the poly I:C+ST7 dosing group. Permutational multivariate analysis of variance (vegan::adonis, 1000 permutations) revealed a significant difference in beta diversity, which was quantified using the betadisper function (vegan::betadisper, 1000 permutations). Both adonis and betadisper indices yielded P values of <0.05 and >0.05, respectively.

Figure 7:
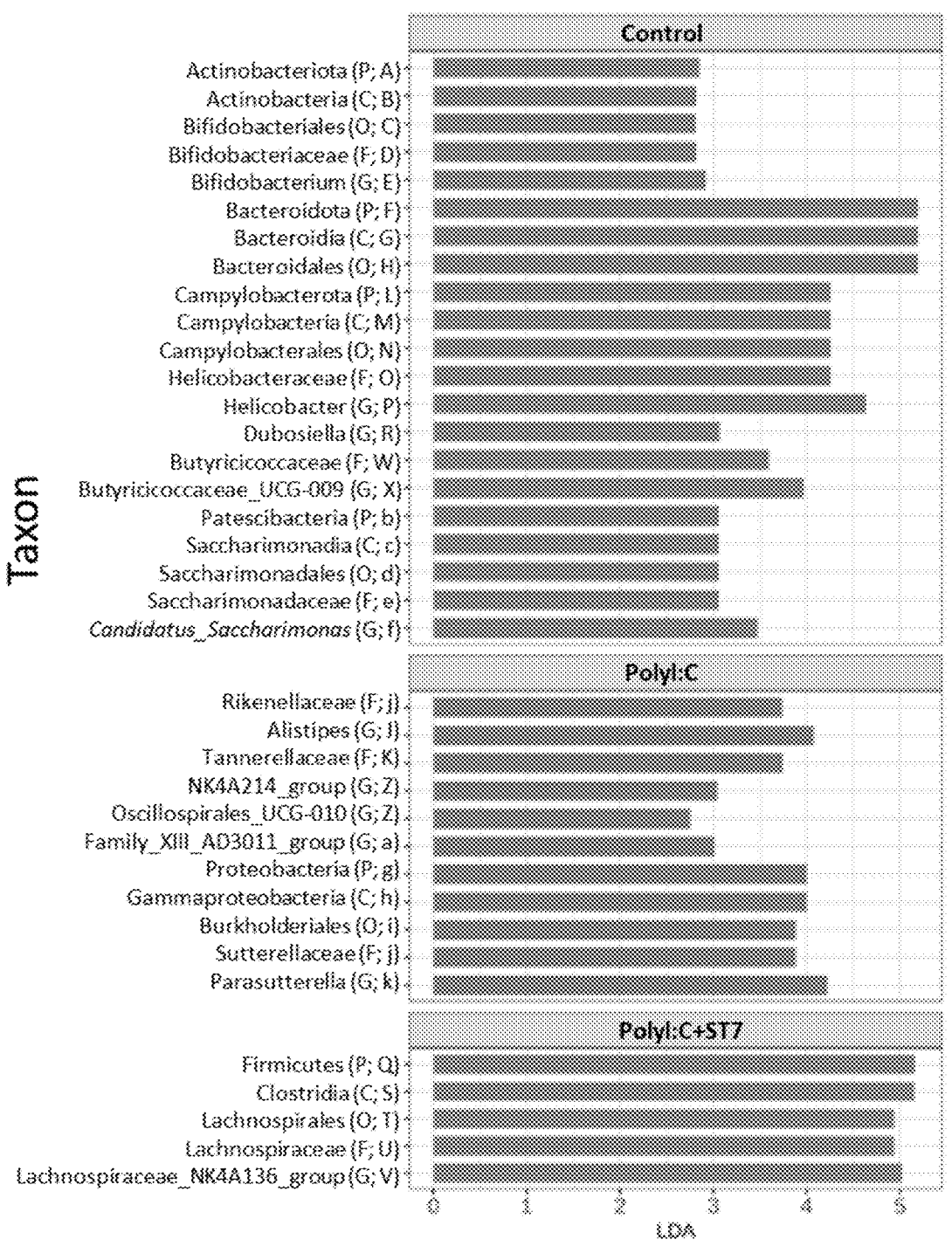
FIG. 7 shows the microbial taxa with significantly differ-
ent abundances in animal experiments demonstrating the
effect of *Streptococcus thermophilus* ST7 on the intestinal
microbiota.

Referring to FIG. 7, it shows the effect of *Streptococcus thermophilus* ST7 on the microbial taxa of the intestinal microbiota, which was analyzed using LEfSe, wherein significant taxon differences were defined as LDA scores (log $10) \geq 2$, *P<0.05. FIG. 7 shows that the control group had higher LDA scores for Actinobacteriota, Bacteroidota, Campilobacterota, and Patescibacteria at the phylum level. Compared with the control group, the poly I:C group had higher LDA scores for Proteobacteria at the phylum level, Gammaproteobacteria at the class level, and *Alistipes* at the genus level. Compared with the poly I:C group, the ST7+ poly I:C group had higher LDA scores for Firmicutes at the phylum level, Clostridia at the class level, and Lachnospirales at the order level.

Figure 8:
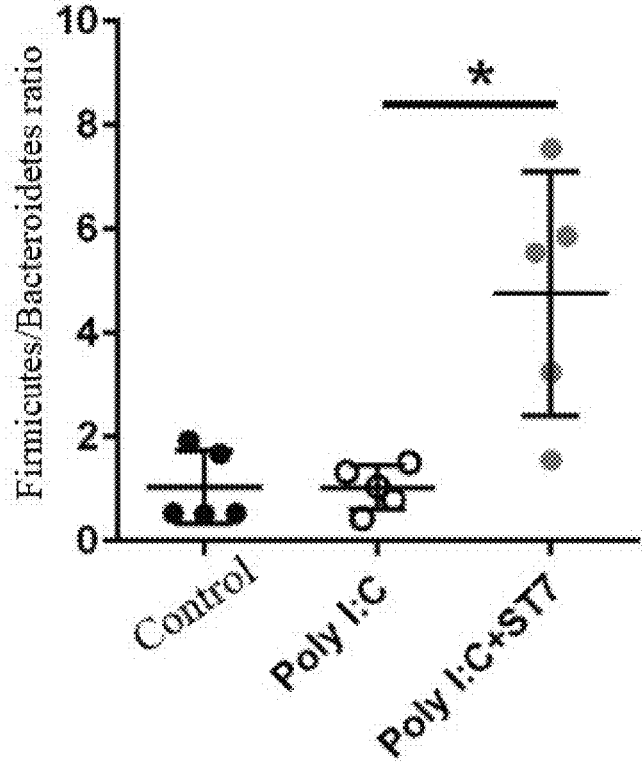
FIG. 8 shows the Firmicutes/Bacteroidetes ratio in animal
experiments demonstrating the effect of *Streptococcus ther-
mophilus* ST7 on the intestinal microbiota.

Referring to FIG. 8, it shows the effect of *Streptococcus thermophilus* ST7 on the Firmicutes/Bacteroidetes ratio in the intestinal microbiota. The Firmicutes/Bacteroidetes ratio is a factor for measuring the risk of a specific disease in recent microorganism studies. A lower Firmicutes/Bacteroidetes ratio is usually observed in intestinal inflammatory diseases. FIG. 8 shows that the Firmicutes/Bacteroidetes ratio was low in the viral infection group treated with poly I:C, while in the poly I:C+ST7 dosing group, the administration of *Streptococcus thermophilus* ST7 significantly increased the Firmicutes/Bacteroidetes ratio. It is indicated that the *Streptococcus thermophilus* strain ST7 of the present invention can change the intestinal microbiota and alleviate intestinal inflammatory diseases.

In summary, since intestinal microbiota imbalance is simultaneously associated with inflammation and infection, it is generally believed that live probiotics have the potential to modulate the intestinal microbiota and ameliorate enteritis. However, this experiment unexpectedly found the heat-killed *Streptococcus thermophilus* strain ST7 can modulate the intestinal microbiota after poly I:C induced enteritis. That is, the inactivated bacteria of the *Streptococcus thermophilus* strain ST7 of the present invention can improve microbial dysbiosis in mice with virus-induced intestinal injury.

Embodiment 8: Activation of CD4+ T Cells and CD8+ T Cells Improved by *Streptococcus thermophilus* ST7 During Viral Infection In order to illustrate the effect of the *Streptococcus thermophilus* strain ST7 of the present invention on immune cells, this experiment was carried out using flow cytometry. Cell surface molecules were stained with specific antibodies and then analyzed by a flow cytometer. The following antibodies were used in conjugation with a fluorochrome from BioLegend: CD3-FITC (2C11), CD8α-APC-Cy7 (53-6.7), CD19-PB (6D5), CD4-PE-Cy7 (GK1.5), and CD69-PE (H1.2F3). The above experiment was used to detect the CD69 expression after poly I:C stimulation thereby investigating whether *Streptococcus thermophilus* ST7 can modulate T cell activation.

Figure 9:
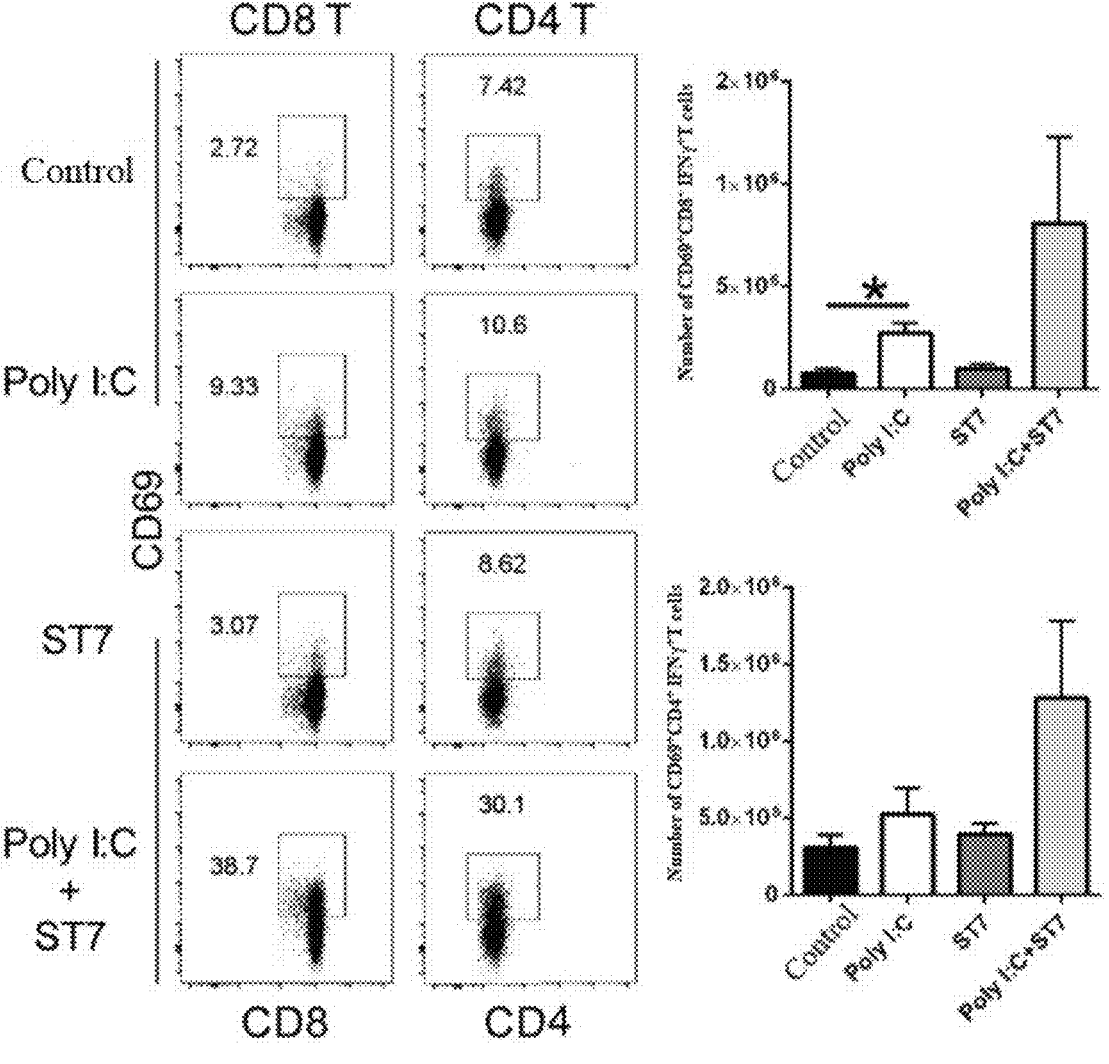
FIG. 9 shows the effect of *Streptococcus thermophilus*
ST7 on the activation of spleen $CD8^+$ T cells and $CD4^+$ T
cells in animal experiments.

Referring to FIG. 9, it shows that *Streptococcus thermophilus* ST7 affects the activation of spleen CD8+ T cells and CD4+ T cells, n=5, *P<0.05. As shown in the figure, feeding *Streptococcus thermophilus* ST7 alone did not affect the counts of the spleen CD69+ CD8+ T cells and CD69+ CD4+ T cells; however, in the poly I:C+ST7 dosing group, an increase in the counts of CD69+ CD8+ T cells and CD69+ CD4+ T cells was observed. It is demonstrated that when stimulated with poly I:C, *Streptococcus thermophilus* ST7 can promote the activation of spleen CD8+ T cells and CD4+ T cells, thereby improving the immunity and antiviral ability.

Embodiment 9: Expression of IFN-γ in CD4+ T Cells and CD8+ T Induced by *Streptococcus thermophilus* ST7

IFN-γ is a key antiviral cytokine. For illustrating the effect of the *Streptococcus thermophilus* strain ST7 of the present invention on the IFN-γ expression, the IFN-γ expression in spleen CD4+ T cells and CD8+ T cells was measured after 2 h of poly I:C or PBS injection in each group of mice.

Figure 10:
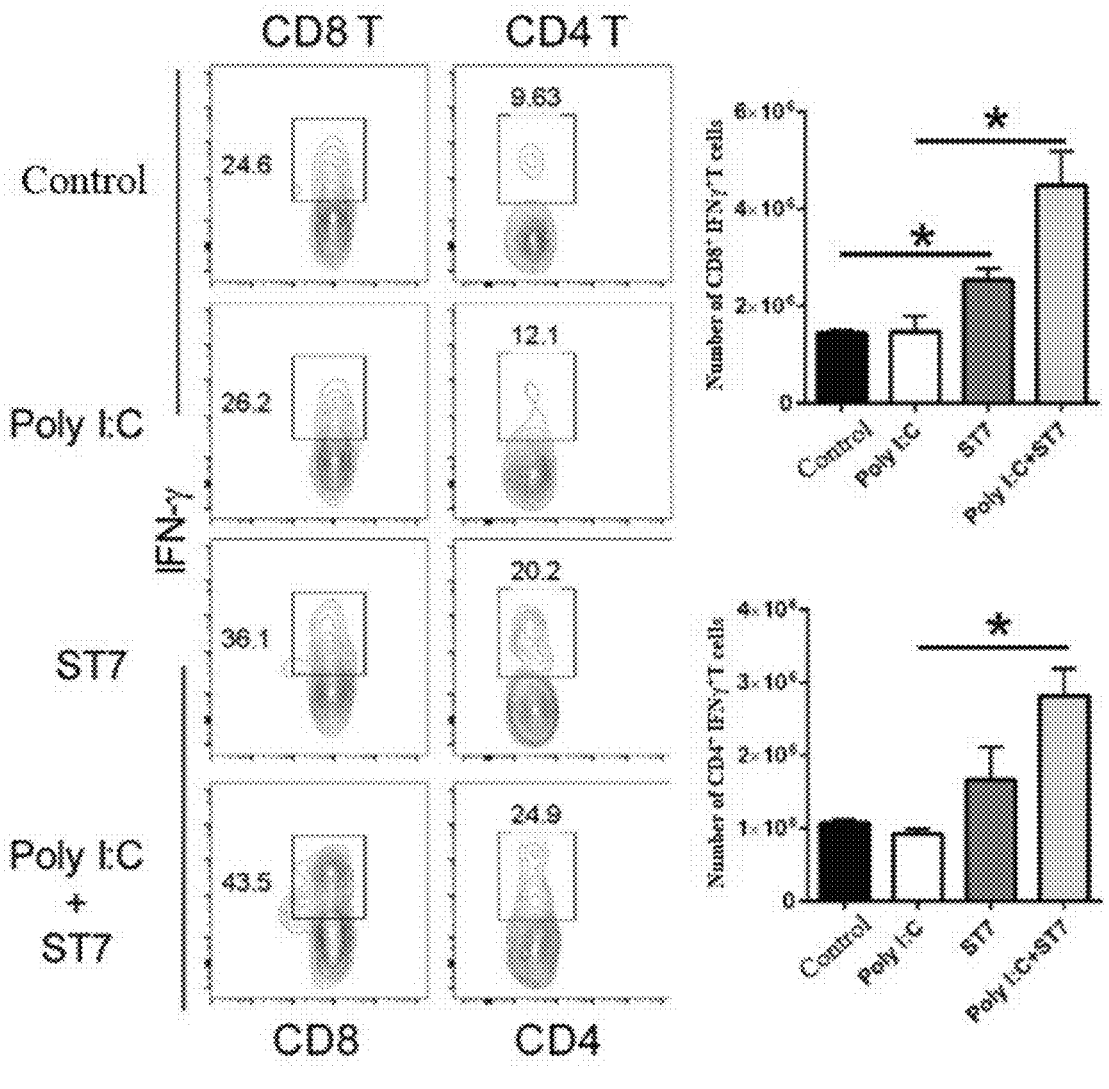
FIG. 10 shows the effect of *Streptococcus thermophilus*
ST7 on the expression of IFN-γ in spleen $CD8^+$ T cells and
$CD4^+$ T cells in animal experiments.

Referring to FIG. 10, it shows that *Streptococcus thermophilus* ST7 affects the IFN-γ expression in spleen CD8+ T cells and CD4+ T cells, n=5, *P<0.05. As shown in the figure, after 2 h of poly I:C stimulation, the expression level of IFN-γ in spleen CD8+ T cells and CD4+ T cells did not change. However, surprisingly the administration of *Streptococcus thermophilus* ST7 alone significantly increased the expression level of IFN-γ in spleen CD8+ T cells and CD4+ T cells, and the effect was stronger in the presence of poly I:C. It is indicated that regardless of whether there is poly I:C stimulation, *Streptococcus thermophilus* ST7 can promote the IFN-γ expression in spleen CD8+ T cells and CD4+ T cells after poly I:C stimulation and thereby improve immunity and antiviral ability.

In summary, the intake of *Streptococcus thermophilus* ST7 can induce the antiviral ability of CD4+ T cells and CD8+ T cells, and also enhance the activation of CD4+ T cells and CD8+ T cells during the poly I:C stimulation, demonstrating good ability to prevent and alleviate viral infections and related symptoms.

The *Streptococcus thermophilus* strain ST7 of the present invention has the following characteristics:

(1) *Streptococcus thermophilus* ST7 has an outstanding effect in inducing IL-12p40 over other *Streptococcus thermophilus* strains.

(2) Inactivated *Streptococcus thermophilus* ST7 has an enhanced effect, which is obviously different from other *Streptococcus thermophilus* strains.

(3) The intake of *Streptococcus thermophilus* ST7 (in particular inactivated bacteria) has the ability to modulate intestinal microbiota and increases a Firmicutes/Bacteroidetes ratio in the intestine.

(4) The intake of *Streptococcus thermophilus* ST7 (in particular inactivated bacteria) can improve the antiviral ability, increase the expression level of serum IFN-γ, and induce the expression of IFN-γ in CD4+ T cells and CD8+ T cells, as well as increase the activation of CD4+ T cells and CD8+ T cells during viral infection thereby promoting the antiviral function of T cells.

The above specific illustrations are specific descriptions of feasible examples of the present invention. However, these examples are not intended to limit the patent scope of the present invention. Any equivalent embodiment or modification that does not depart from the technical spirit of the present invention shall be included within the scope of the patent application.

The above-mentioned multiple efficacies fully meet the statutory requirements of novelty and an inventive step for a patent. An application for the invention is filed in accordance with the law and the patent office is kindly asked to grant this application to encourage invention.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for modulating immunity in an individual, comprising administering *Streptococcus thermophilus* ST7, wherein the *Streptococcus thermophilus* ST7 is an active ingredient that modulates immunity, wherein the *Streptococcus thermophilus* ST7 is deposited at the German Collection of Microorganisms and Cell cultures under accession no. DSM34255, wherein the modulating immunity is increasing the expression level of IL12p40 in cells to between 400 and 1000 μg/mL, increasing the ratio of Firmicutes to Bacteroidetes in the intestinal microbiota, alleviating intestinal injury caused by viruses and enhancing antiviral immunity, increasing the activation of CD4$^+$ T cells and CD8$^+$ T cells during viral infection, or inducing the expression of IFN-γ in the CD4+ T cells and CD8+ T cells.

2. The method according to claim 1, wherein the *Streptococcus thermophilus* ST7 is an inactivated bacterium.

3. The method according to claim 1, wherein no other strains of bacteria besides *Streptococcus thermophilus* ST7 are administered.

4. The method according to claim 1, wherein the *Streptococcus thermophilus* ST7 is administered at a dose of 1×10$^6$ to 1×10$^{10}$ CFU/day.

* * * * *